United States Patent
Figge et al.

(10) Patent No.: US 9,023,624 B2
(45) Date of Patent: May 5, 2015

(54) FERMENTATIVE PRODUCTION OF METHIONINE HYDROXY ANALOG (MHA)

(75) Inventors: Rainer Figge, Le crest (FR); Wanda Dischert, Vics-le-Comte (FR)

(73) Assignee: Metabolic Explorer, Saint Beauzire (FR)

( * ) Notice: Subject to any disclaimer, the term of this patent is extended or adjusted under 35 U.S.C. 154(b) by 0 days.

(21) Appl. No.: 13/995,909

(22) PCT Filed: Dec. 30, 2010

(86) PCT No.: PCT/IB2010/003516
§ 371 (c)(1),
(2), (4) Date: Oct. 2, 2013

(87) PCT Pub. No.: WO2012/090022
PCT Pub. Date: Jul. 5, 2012

(65) Prior Publication Data
US 2014/0017740 A1    Jan. 16, 2014

(51) Int. Cl.
C12P 13/00      (2006.01)
C12P 11/00      (2006.01)
C12P 13/12      (2006.01)

(52) U.S. Cl.
CPC ....... *C12P 11/00* (2013.01); *C12P 13/12* (2013.01)

(58) Field of Classification Search
None
See application file for complete search history.

(56) References Cited

U.S. PATENT DOCUMENTS

| | | | |
|---|---|---|---|
| 2,745,745 A | 5/1956 | Blake et al. | |
| 2,938,053 A | 5/1960 | Blake et al. | |
| 3,175,000 A | 3/1965 | Gielkens | |
| 4,175,121 A | 11/1979 | Mantha | |
| 4,353,924 A | 10/1982 | Baker et al. | |
| 6,180,359 B1 | 1/2001 | Favre-Bulle et al. | |
| 8,389,250 B2 | 3/2013 | Figge et al. | |
| 2008/0311632 A1 | 12/2008 | Figge et al. | |
| 2009/0029424 A1 | 1/2009 | Bestel-Corre et al. | |
| 2009/0181001 A1 | 7/2009 | Takano et al. | |
| 2010/0248311 A1 | 9/2010 | Figge | |

FOREIGN PATENT DOCUMENTS

| | | |
|---|---|---|
| EP | 0142488 A2 | 5/1985 |
| EP | 0143000 A1 | 5/1985 |
| EP | 1358805 A1 | 11/2003 |
| FR | 2920967 A1 | 3/2009 |
| WO | 9832872 A1 | 7/1998 |
| WO | 2005111202 A1 | 11/2005 |
| WO | 2007051725 A2 | 5/2007 |
| WO | 2007077041 A1 | 7/2007 |
| WO | 2007112433 A2 | 10/2007 |
| WO | 2009042272 A1 | 4/2009 |
| WO | 2009043372 A1 | 4/2009 |
| WO | 2009043803 A2 | 4/2009 |
| WO | 2009088879 A1 | 7/2009 |
| WO | 2011073738 A1 | 6/2011 |

OTHER PUBLICATIONS

International Search Report for PCT/IB2010/003216 Mailed September 20, 2011.
Anderson Growth Requirements of Virus-Resistant Mutants of *Escherichia coli* Strain "B", Proc. Natl. Acad. Sci., vol. 32 (1946) p. 120-128.
Carrier "Library of Synthtic 5' Secondary Structures to Manipulate MRNA Stability in *Escherichia coli*", Biotechnol. Prog., vol. 15 (1999) p. 58-64.
Datsenko et al. "One-Step Inactivation of Chromosomal Genes in *Escherichia coli* K-12 Using PCR Products", Proc. Natl. Acad. Sci., vol. 97. No. 12 (2002) p. 6640-6645.
Liebl et al. "Requirement of Chelating Compounds for the Growth of *Corynebacterium* Glatamicum in Synthetic Media", Appl. Microbiol. Biotechnol., vol. 32 (1989) p. 205-210.
Riedel et al. "Characterization of the Phosphoenolpyruvate Carboxykinase Gene From *Corynebacterium* Glutamicum and Significance of the Enzyme for Growth and Amino Acid Production", J. Mol. Microbiol. Biotechnol., vol. 3 (2001) p. 573-583.
Schaefer et al. "Automated Sampling Device for Monitoring Intracellular Metabolite Dynamics", Analytical Biochemistry, vol. 270 (1999) p. 88-96.
Dischert, U.S. Appl. No. 61/406,249, filed October 25, 2010.

*Primary Examiner* — Nashaat Nashed
(74) *Attorney, Agent, or Firm* — Miles & Stockbridge P.C.

(57) ABSTRACT

The present invention is related to a method for the fermentative production of hydroxymethionine, comprising the steps of:
culturing a recombinant microorganism modified to produce methionine in an appropriate culture medium comprising a source of carbon, a source of sulfur and a source of nitrogen,
recovering hydroxymethionine from the culture medium.
In a specific embodiment, the recombinant microorganism is cultivated under conditions of nitrogen limitation.
The invention is also related to the biologically-produced hydroxymethionine and its uses.

12 Claims, 1 Drawing Sheet

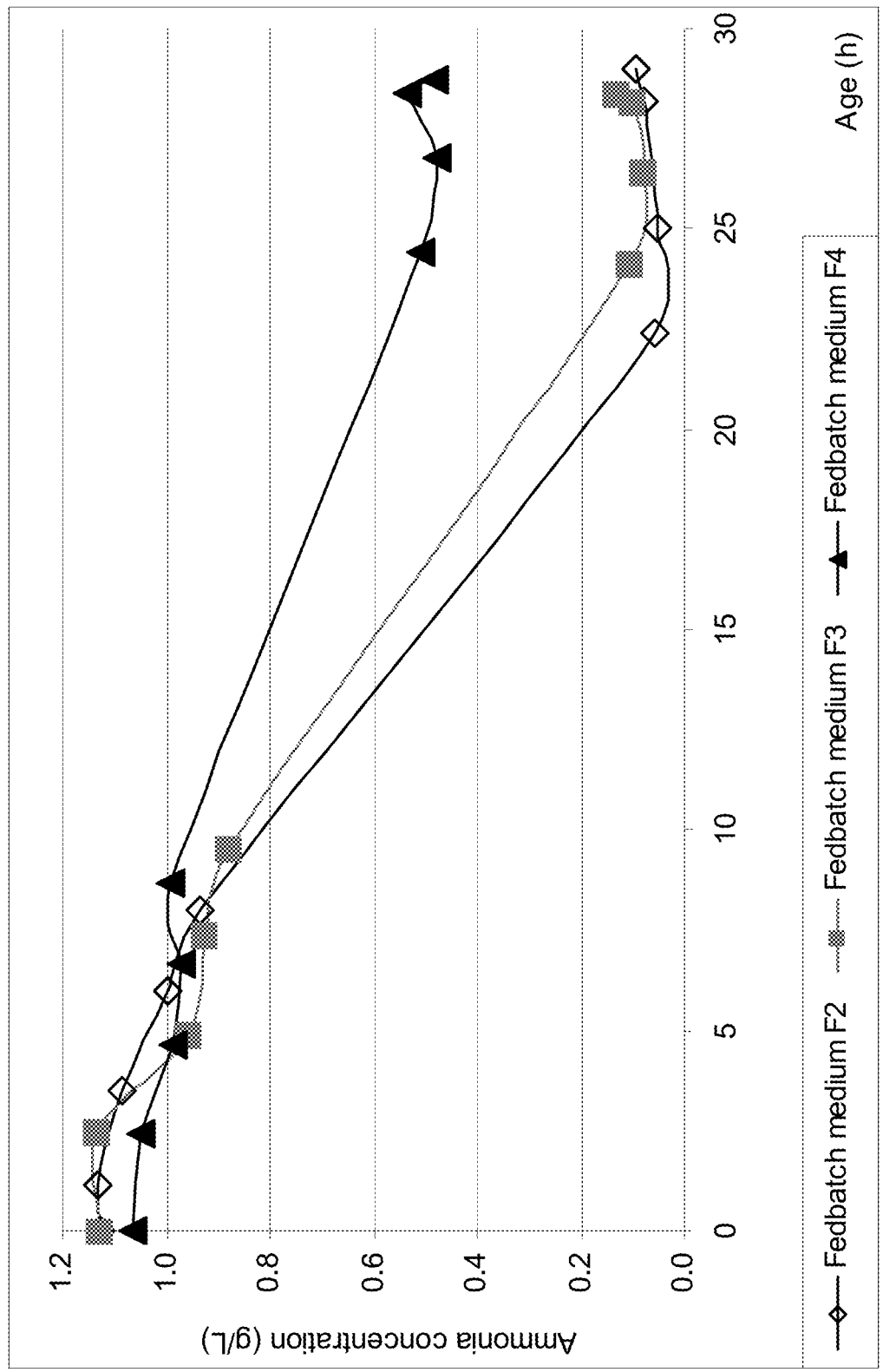

FERMENTATIVE PRODUCTION OF METHIONINE HYDROXY ANALOG (MHA)

CROSS REFERENCE TO RELATED APPLICATIONS

This application is a §371 National Stage Application of PCT/IB2010/003516, filed Dec. 30, 2010.

BACKGROUND OF THE INVENTION

1. Field of the Invention

The present invention relates to a method for producing 2-hydroxy-4-(methylthio) butyric acid (HMBA) an analog of the essential amino acid methionine, by fermentation. Fermentation is a biological process wherein a microorganism, using the carbon, sulphur and nitrogen provided in the culture medium, bio-synthesizes a product of interest that is usually chemically synthesized.

2. Description of Related Art

2-Hydroxy-4-(methylthio) butyric acid (HMBA), commonly referred to as "hydroxymethionine" is an analog of the essential amino acid methionine, and an important feed additive. It is commonly used in poultry diets because methionine in commercial corn-soybean-based feedstuffs is considered to be the first limiting amino acid.

The methionine hydroxy analog contains a hydroxyl radical on the α-carbon of the methionine molecule rather than an amino group. HMBA has the formula:

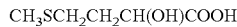

$CH_3SCH_2CH_2CH(OH)COOH$

In contrast with the amino acid, it is not used directly by the organism in protein synthesis, because it must be anabolically converted into the amino acid to be used as such. HMBA is not used in the pure form, but in various forms, namely:
- a mixture of calcium and ammonium salts of HMBA (U.S. Pat. No. 2,745,745 and U.S. Pat. No. 2,938,053),
- acidic aqueous solutions (U.S. Pat. No. 4,353,924),
- calcium salts of HMBA, obtained by the process described in U.S. Pat. No. 3,175,000.

The preparation of HMBA by a chemical route has been known for a long time. Several patents from NOVUS International (PCT/US98/01595), MONSANTO Company (EP0142488), BRITISH Telecomm (EP0143000) or Rhone Poulenc Animal Nutrition S.A. (U.S. Pat. No. 6,180,359) describe hydrolysis of 2-hydroxy-4-methylthio-hydroxybutyronitrile (HMBN) into HBMA by a two-stage process. All these technologies rely approximately on the same raw material and key intermediates.

The first stage consists in bringing the 2-hydroxy-4-methylthiobutyronitrile (HMBN) into contact with strong inorganic acid such as hydrochloric or sulphuric acid. In a subsequent stage, after dilution with water, the hydrolysis is completed at a higher temperature. The HMBA is then extracted with organic solvent which is not very miscible with water, such as ketone, and then the solvent is removed by evaporation.

The amide 2-hydroxy-4-methylthio-butyronitrile (HMBN) is synthetized by reaction between methyl-mercapto-propionaldehyde (MMP) and hydrocyanic acid (HCN) or sodium cyanide (NaCN).

During the past few years, new methods have emerged involving enzymes or biological material. Aventis Animal Nutrition S. A. has for instance described and patented a method for the preparation of HMBA by enzymatic hydrolysis of the 2-hydroxy-4-methylthiobutyronitrile intermediate. The invention is based on bioconversion of HMBN after contacting the molecule with immobilized biological material having nitrilase activity (U.S. Pat. No. 6,180,359). A similar process was described by Novus with the enzymatic conversion of 2-hydroxy-4-(methylthio)-butanenitrile to 2-hydroxy-4-(methylthio)-butaneamide or 2-hydroxy-4-(methylthio)-butanoic acid or salts (WO 1998032872).

In their efforts to improve the production of methionine by microorganisms, inventors have surprisingly found that hydroxymethionine can be also produced in microorganism from a simple carbon source in a fermentative process. This is the first report of a fully biological production of methionine hydroxy analog.

SUMMARY

The invention is related to a method for the fermentative production of hydroxymethionine, comprising the steps of:
- culturing a recombinant microorganism modified to produce methionine in an appropriate culture medium, comprising a source of carbon, a source of sulfur and a source of nitrogen,
- recovering hydroxymethionine from the culture medium.

The fermentative production is based on the growth of microorganisms, wherein a simple source of carbon, usually a sugar, is used by the microorganisms both for their growth and for the biosynthesis of a compound of interest.

BRIEF DESCRIPTION OF THE DRAWING

FIG. 1 represents embodiments as described herein.

DETAILED DESCRIPTION OF A PREFERRED EMBODIMENT

The present invention is related to a method for producing hydroxymethionine, wherein a recombinant microorganism optimized for the production of methionine produce hydroxymethionine from a source of carbon, a source of sulfur and a source of nitrogen.

Product

The terms "hydroxymethionine" or "methionine hydroxy analog" or "MHA" or "2-Hydroxy-4-(methylthio) butyric acid" or "2-Hydroxy-4-(methylthio) butanoic acid" or "HMTBA" or "HMBA" or "DL-2-Hydroxy-4-(methylmercapto) butanoic acid" are used interchangeably to designate the fermentation product.

Microorganisms

The present invention is related to the use of a microorganism optimized for the production of methionine, for producing hydroxymethionine.

The terms "microorganism for the production of methionine" or "methionine-producing microorganism" or "microorganism modified to produce methionine" or "microorganism optimized for the production of methionine" designate a microorganism producing higher levels of methionine than non-producing microorganisms, which produce methionine only for their endogenous needs, when the modified microorganism produces more methionine than needed by the microorganism's metabolism. Microorganisms optimized for methionine production are well known in the art, and have been disclosed in particular in patent applications US2009029424 A1, US2008311632 A1 and US2010248311 A1.

The term "recombinant microorganism" or "modified microorganism" designates a microorganism genetically modified, by addition or suppression of genes, or modification of the regulation of the expression of some genes.

According to the invention, the amount of methionine produced by the recombinant microorganism, and particularly the methionine yield (ratio of gram/mol methionine produced per gram/mol carbon source), is higher in the modified microorganism compared to the corresponding unmodified microorganism. Usual modifications include deletions of genes by transformation and recombination, gene replacements, and overexpression of genes or introduction of vectors for the expression of heterologous genes.

These microorganisms optimized for methionine production are able to produce hydroxymethionine at the same time. The inventors have observed that if more methionine is produced by the microorganisms, also more hydroxymethionine is produced.

The microorganism used in the invention is a bacterium, a yeast or a fungus. Preferentially, the microorganism is selected among Enterobacteriaceae, Bacillaceae, Streptomycetaceae and Corynebacteriaceae. More preferentially, the microorganism is of the genus *Escherichia, Klebsiella, Pantoea, Salmonella* or *Corynebacterium*. Even more preferentially, the microorganism is either the species *Escherichia coli* or *Corynebacterium glutamicum*.

Fermentation

The terms "fermentative process", 'culture' or "fermentation" are used interchangeably to denote the growth of bacteria on an appropriate growth medium containing a simple carbon source, a source of sulphur and a source of nitrogen.

In the fermentative process of the invention, the source of carbon is used simultaneously for:
 biomass production: growth of the microorganism by converting inter alia the carbon source of the medium, and,
 hydroxymethionine and/or methionine production: transformation of the same carbon source into hydroxymethionine and/or methionine by the biomass.

The two steps are concomitant, and the transformation of the source of carbon by the microorganism to grow results in the hydroxymethionine and/or methionine production in the medium, since the microorganism comprises a metabolic pathway allowing such conversion.

Fermentation is a classical process that can be performed under aerobic, microaerobic or anaerobic conditions.

The fermentation is generally conducted in fermenters with an appropriate culture medium adapted to the microorganism being used, containing at least one simple carbon source, and if necessary co-substrates for the production of metabolites.

In the invention, the fermentation is done in fed-batch mode. This refers to a type of fermentation in which supplementary growth medium is added during the fermentation, but no culture is removed until the end of the batch (except small volumes for samplings and HPLC/GCMS analysis). The process comprises two main steps; the first one which is a series of pre cultures in appropriate batch mineral medium and fed-batch mineral medium. Subsequently, a fermentor filled with appropriate minimal batch medium is used to run the culture with different fedbatch medium according to the desire production.

Those skilled in the art are able to define the culture conditions and the composition of culture medium for the microorganisms according to the invention. In particular the bacteria are fermented at a temperature between 20° C. and 55° C., preferentially between 25° C. and 40° C., and more specifically about 30° C. for *C. glutamicum* and about 37° C. for *E. coli*.

As an example of known culture medium for *E. coli*, the culture medium can be of identical or similar composition to an M9 medium (Anderson, 1946, *Proc. Natl. Acad. Sci. USA* 32:120-128), an M63 medium (Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.) or a medium such as defined by Schaefer et al. (1999, *Anal. Biochem.* 270: 88-96).

As an example of known culture medium for *C. glutamicum*, the culture medium can be of identical or similar composition to BMCG medium (Liebl et al., 1989, *Appl. Microbiol. Biotechnol.* 32: 205-210) or to a medium such as described by Riedel et al. (2001, *J. Mol. Microbiol. Biotechnol.* 3: 573-583).

The term "source of carbon" according to the invention denotes any source of carbon that can be used by those skilled in the art to support the normal growth of a microorganism, which can be hexoses such as glucose, galactose or lactose; pentoses; monosaccharides; disaccharides such as sucrose (molasses), cellobiose or maltose; oligosaccharides such as starch or its derivatives; hemicelluloses; glycerol and combinations thereof. An especially preferred carbon source is glucose. Another preferred carbon source is sucrose.

In a particular embodiment of the invention, the carbon source is derived from renewable feed-stock. Renewable feed-stock is defined as raw material required for certain industrial processes that can be regenerated within a brief delay and in sufficient amount to permit its transformation into the desired product. Vegetal biomass treated or not, is an interesting renewable carbon source.

The source of carbon is fermentable, i.e. it can be used for growth by microorganisms.

The term "source of sulphur" according to the invention refers to sulphate, thiosulfate, hydrogen sulphide, dithionate, dithionite, sulphite, methylmercaptan, dimethylsulfide and other methyl capped sulphides or a combination of the different sources. More preferentially, the sulphur source in the culture medium is sulphate or thiosulfate or a mixture thereof.

The culture may be performed in such conditions that the microorganism is limited or starved for an inorganic substrate, in particular phosphate and/or potassium. Subjecting an organism to a limitation of an inorganic substrate defines a condition under which growth of the microorganisms is governed by the quantity of an inorganic chemical supplied that still permits weak growth. Starving a microorganism for an inorganic substrate defines the condition under which growth of the microorganism stops completely due, to the absence of the inorganic substrate.

The term "source of nitrogen" corresponds to either an ammonium salt or ammoniac gas. Nitrogen comes from an inorganic (e.g., $(NH_4)_2SO_4$) or organic (e.g., urea or glutamate) source. In the invention sources of nitrogen in culture are $(NH_4)_2HPO_4$, $(NH4)2S2O3$ and $NH_4OH$.

In a specific aspect of the invention, the recombinant microorganism is cultivated under conditions of nitrogen limitation. Indeed, the inventors have observed that conditions of nitrogen limitation enhance hydroxymethionine production.

The term "conditions of nitrogen limitation" refers to a culture medium having a limited concentration of nitrogen, wherein the nitrogen may be supplied from an inorganic (e.g., $(NH_4)_2SO_4$) or organic (e.g., urea or glutamate) source, and the term "conditions of nitrogen starvation" refers to a medium having no nitrogen source at all.

"Nitrogen limitation" means that the available nitrogen source is present in an amount such that the rate of growth and/or biomass yield of the bacterium is limited, i.e. the nitrogen source is present in an amount below the necessary amount to support the maximal growth rate and/or biomass yield. A man skilled in the art will be able to determine an appropriate limited concentration of nitrogen suitable to induce the production of hydroxymethionine. The actual "nitrogen limiting amount" may vary with the particular media and with the microorganism strain used. For instance, the microorganism is a recombinant bacterium producing methionine and hydroxymethionine with a high nitrogen need. The amount of nitrogen applied in the medium is dependent of these characteristics. It may be determined by routine experimentation with the bacterium in media under different concentrations of the nitrogen source. Moreover the man skilled in the art knows methods, such as ionic chromatography, to measure the concentration of available nitrogen in the medium during fermentation, and so the residual nitrogen concentration to determine the conditions of the limitation.

It is known that the growth of a non modified *E. coli* strain in normal conditions requires a ratio C/N (mole/mole) of about 4.2 (Energetics and kinetics in biotechnology. J. A. Roels. Elsevier Science & Technology (May 1983)).

In a specific embodiment of the invention, the fermentation is conducted in general conditions wherein the different media used in the culture lead to a C/N molar ratio greater than about 5, preferably greater than about 10, more preferably greater than about 20 and most preferably between about 20 and about 25 (wherein the C/N ratio is measured as the molar ratio of elemental carbon to elemental nitrogen in the respective carbohydrate and nitrogen sources).

In a preferred embodiment of the invention, the process of production comprises three successive steps with the same microorganism in the same culture batch medium:
   growing a recombinant microorganism in an appropriate culture medium comprising a fermentable source of carbon, a source of sulphur and a source of nitrogen,
   culturing the recombinant microorganism under conditions of nitrogen limitation in said appropriate culture medium,
   recovering hydroxymethionine from the culture medium.

The fermentation is performed in the same original batch medium during all the process wherein culture conditions evolve, depending on microorganism performances and composition of fed-batch medium brought during the culture.

The step of 'growth' is performed in minimal medium conditions without limitation wherein production of methionine starts. The step of 'culture', wherein the production of hydroxymethionine is enhanced, is performed under conditions of nitrogen limitation. The nitrogen limitation occurs when the microorganism consumed almost all the nitrogen present in the culture medium for its division and production. The more the microorganism grows and produces methionine, the more it uses nitrogen. Thus the conditions of nitrogen limitation depend on the characteristics of the microorganism and more precisely on its growth and production rate. The man skilled in the art is able to calculate and foresee specific needs of a recombinant microorganism.

In a specific embodiment of the invention, the recombinant microorganism is cultivated in a bio-reactor system in two successive steps:
   a. Growth of the microorganisms for about 10 h to 20 h in an appropriate culture medium comprising a fermentable source of carbon, a source of sulphur and nitrogen, preferably for about 15 h to 20 h,
   b. Culture of the microorganisms for about 10 h to 20 h in nitrogen limitation conditions in said appropriate culture medium, preferably for about 10 h to 15 h.

As previously described, the recombinant microorganism used in the process according to the invention is genetically modified for converting the source of carbon into methionine and hydroxymethionine.

Genetic Modifications

In the description of the present invention, genes and proteins are identified using the denominations of the corresponding genes in *E. coli*. However, and unless specified otherwise, use of these denominations has a more general meaning according to the invention and covers all the corresponding genes and proteins in other organisms, more particularly microorganisms.

PFAM (protein families database of alignments and hidden Markov models available on the SANGER website) represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins available on the National Center for Biotechnology Information (NCBI) website are obtained by comparing protein sequences from 66 fully sequenced genomes representing 38 major phylogenic lines. Each COG is defined from at least three lines, which permits the identification of former conserved domains.

The means of identifying homologous sequences and their percentage homologies are well known to those skilled in the art, and include in particular the BLAST programs, which can be used from the website of National Center for Biotechnology Information (NCBI) with the default parameters indicated on that website. The sequences obtained can then be exploited (e.g., aligned) using, for example, the programs CLUSTALW (available on the European Bioinformatics Institute (EBI) website or MULTALIN (available on the INRA website, with the default parameters indicated on those websites.

Using the references given in GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are claimed, for example, in Sambrook et al. (1989 Molecular Cloning: a Laboratory Manual. $2^{nd}$ ed. Cold Spring Harbor Lab., Cold Spring Harbor, N.Y.).

The term "attenuation of activity" according to the invention could be employed for an enzyme or a gene and denotes, in each case, the partial or complete suppression of the expression of the corresponding gene, which is then said to be 'attenuated'. This suppression of expression can be either an inhibition of the expression of the gene, a deletion of all or part of the promoter region necessary for the gene expression, a deletion in the coding region of the gene, or the exchange of the wildtype promoter by a weaker natural or synthetic promoter. Preferentially, the attenuation of a gene is essentially the complete deletion of that gene, which can be replaced by a selection marker gene that facilitates the identification, isolation and purification of the strains according to the invention. A gene is inactivated preferentially by the technique of homologous recombination (Datsenko, K. A. & Wanner, B. L. (2000) "One-step inactivation of chromosomal genes in *Escherichia coli* K-12 using PCR products". Proc. Natl. Acad. Sci. USA 97: 6640-6645).

The term "enhanced activity" designates an enzymatic activity that is superior to the enzymatic activity of the non modified microorganism. The man skilled in the art knows how to measure the enzymatic activity of said enzyme.

To enhance an enzymatic activity, the man skilled in the art knows different means: modifying the catalytic site of the protein, increasing the stability of the protein, increasing the stability of the messenger RNA, increasing the expression of the gene encoding the protein.

Elements stabilizing the proteins are known in the art (for example the GST tags, Amersham Biosciences), as well as elements stabilizing the messenger RNA (Carrier and Keasling (1998) Biotechnol. Prog. 15, 58-64).

The terms "increased expression of the gene", "enhanced expression of the gene" or "overexpression of the gene" are used interchangeably in the text and have similar meaning.

To increase the expression of a gene, the man skilled in the art knows different techniques: increasing the copy-number of the gene in the microorganism, using a promoter inducing a high level of expression of the gene, attenuating the activity and/or the expression of a direct or indirect transcription repressor of the gene.

The gene is encoded chromosomally or extrachromosomally. When the gene is located on the chromosome, several copies of the gene can be introduced on the chromosome by methods of recombination known to the expert in the field (including gene replacement). When the gene is located extra-chromosomally, the gene is carried by different types of plasmids that differ with respect to their origin of replication and thus their copy number in the cell. These plasmids are present in the microorganism in 1 to 5 copies, or about 20 copies, or up to 500 copies, depending on the nature of the plasmid: low copy number plasmids with tight replication (pSC101, RK2), low copy number plasmids (pACYC, pRSF1010) or high copy number plasmids (pSK bluescript II).

In a specific embodiment of the invention, the gene is expressed using promoters with different strength. In one embodiment of the invention, the promoters are inducible. These promoters are homologous or heterologous. The man skilled in the art knows which promoters are the most convenient, for example promoters Ptrc, Ptac, Plac or the lambda promoter a are widely used.

Optimization of Methionine Biosynthesis Pathway:

Genes involved in methionine production in a microorganism are well known in the art, and comprise genes involved in the methionine specific biosynthesis pathway as well as genes involved in precursor-providing pathways and genes involved in methionine consuming pathways.

Efficient production of methionine requires the optimisation of the methionine specific pathway and several precursor-providing pathways. Methionine producing strains have been described in patent applications US2009029424 A1, US2008311632 A1 and US2010248311 A1. These applications are incorporated by reference into this application.

The patent application US2009029424 A1 describes a methionine producing strain that overexpresses homoserine succinyltransferase alleles with reduced feed-back sensitivity to its inhibitors SAM and methionine (called metA*). This application describes also the combination of these alleles with a deletion of the methionine repressor MetJ responsible for the down-regulation of the methionine regulon. In addition, the application describes combinations of the two modifications with the overexpression of aspartokinase/homoserine dehydrogenase (coded by the thrA gene).

For improving the production of methionine, the microorganism may exhibit:

an increased expression of at least one gene selected in the group consisting of:
- cysP which encodes a periplasmic sulphate binding protein, as described in US2008311632 A1 and in US2010248311 A1,
- cysU which encodes a component of sulphate ABC transporter, as described in US2008311632 A1 and in US2010248311 A1,
- cysW which encodes a membrane bound sulphate transport protein, as described in US2008311632 A1 and in WUS2010248311 A1,
- cysA which encodes a sulphate permease, as described in US2008311632 A1 and in US2010248311 A1,
- cysM which encodes an O-acetyl serine sulfhydralase, as described in US2008311632 A1 and in US2010248311 A1,
- cysI and cysJ encoded respectively the alpha and beta subunits of a sulfite reductase as described in US2008311632 A1 and in US2010248311 A1. Preferably cysI and cysJ are overexpressed together,
- cysH which encodes an adenylylsulfate reductase, as described in US2008311632 A1 and in US2010248311 A1,
- cysE which encodes a serine acyltransferase, as described in US2008311632 A1,
- serA which encodes a phosphoglycerate dehydrogenase, as described in US2008311632 A1 and in US2010248311 A1,
- serB which encodes a phosphoserine phosphatase, as described in US2008311632 A1 and in US2010248311 A1,
- serC which encodes a phosphoserine aminotransferase, as described in US2008311632 A1 and in US2010248311 A1,
- metA alleles which encode an homoserine succinyltransferases with reduced feed-back sensitivity to S-adenosylmethionine and/or methionine (metA*) as described in US2009029424 A1,
- thrA or thrA alleles which encode aspartokinases/homoserine dehydrogenase with reduced feed-back inhibition to threonine (thrA*), as described in US2010248311 A1 and US2009029424 A1, or an inhibition of the expression of at least one of the following genes:
- pykA which encodes a pyruvate kinase, as described in US2008311632 A1 and in US2010248311 A1,
- pykF which encodes a pyruvate kinase, as described in US2008311632 A1 and in US2010248311 A1,
- purU which encodes a formyltetrahydrofolate deformylase, as described in US2008311632 A1 and in US2010248311 A1,
- yncA which encodes a N-acetyltransferase, as described in US2010047879 A1,
- metJ which encodes for a repressor of the methionine biosynthesis pathway, as described in US2009029424 A1,
- ybdL which encodes an aminotransferase.

or an increasing of the C1 metabolism that leads to an improved methionine production.

According to the invention, "increasing C1 metabolism" relates to the increase of the activity of at least one enzyme involved in the C1 metabolism chosen among MetF, GcvTHP, Lpd, GlyA, MetE or MetH. For increasing enzyme activity, the corresponding genes of these different enzymes may be overexpressed or modified in their nucleic sequence to expressed enzyme with improved activity or their sensitivity to feed-back regulation may be decreased.

In a preferred embodiment of the invention, the one carbon metabolism is increased by enhancing the activity of methylenetetrahydrofolate reductase MetF and/or the activity of glycine cleavage complex GcvTHP and/or the activity of serine hydroxymethyltransferase GlyA.

In a specific embodiment of the invention, the activity of MetF is enhanced by overexpressing the gene metF and/or by optimizing the translation.

In a specific embodiment of the invention, overexpression of metF gene is achieved by expressing the gene under the control of a strong promoter belonging to the Ptrc family promoters, or under the control of an inducible promoter, like a temperature inducible promoter $P_R$ as described in application PCT/FR2009/052520.

According to another embodiment of the invention, optimisation of the translation of the protein MetF is achieved by using a RNA stabiliser. Other means for the overexpression of a gene are known to the expert in the field and may be used for the overexpression of the metF gene.

In a specific embodiment of the invention, genes may be under control of an inducible promoter. Patent application PCT/FR2009/052520 describes a methionine producing strain that expresses a thrA allele with reduced feed-back inhibition to threonine and cysE under the control of an inducible promoter. This application is incorporated as reference into this application.

In a preferred embodiment of the invention, the thrA gene or allele is under control of a temperature inducible promoter.

In a most preferred embodiment, the temperature inducible promoter used belongs to the family of $P_R$ promoters.

In another aspect of the invention, the activity of the pyruvate carboxylase is enhanced. Increasing activity of pyruvate carboxylase is obtained by overexpressing the corresponding gene or modifying the nucleic sequence of this gene to express an enzyme with improved activity. In another embodiment of the invention, the pyc gene is introduced on the chromosome in one or several copies by recombination or carried by a plasmid present at least at one copy in the modified microorganism. The pyc gene originates from *Rhizobium etli, Bacillus subtilis, Pseudomonas fluorescens, Lactococcus lactis* or *Corynebacterium* species.

Other genetic modifications leading to improved methionine production are an increased expression of pntAB and/or an attenuation of udhA as described in patent applications US20130183727 and U.S. 61/406,249.

In a particular embodiment of the invention, the overexpressed genes are at their native position on the chromosome or are integrated at a non-native position. For an optimal methionine production, several copies of the gene may be required, and these multiple copies are integrated into specific loci, whose modification does not have a negative impact on methionine production.

Examples for locus into which a gene may be integrated, without disturbing the metabolism of the cell, are the following:

| Locus | accession number | function |
|---|---|---|
| aaaD | 87081759 | Pseudogene, phage terminase protein A homolog, N-terminal fragment |
| aaaE | 1787395 | Pseudogene, phage terminase protein A homolog, C-terminal fragment |
| afuB | 1786458 | Pseudogene, ferric ABC family transporter permease; C-terminal fragment |
| afuC | 87081709 | predicted ferric ABC transporter subunit (ATP-binding component) |
| agaA | 48994927 | Pseudogene, C-terminal fragment, GalNAc-6-P deacetylase |
| agaW | 1789522 | Pseudogene, N-terminal fragment, PTS system EIICGalNAc |
| alpA | 1788977 | protease |
| appY | 1786776 | DNA-binding transcriptional activator |
| argF | 1786469 | ornithine carbamoyltransferase |
| argU | none | arginine tRNA |
| argW | none | Arginine tRNA(CCU) 5 |
| arpB | 87081959 | Pseudogene reconstruction, ankyrin repeats |
| arrD | 1786768 | lysozyme |
| arrQ | 1787836 | Phage lambda lysozyme R protein homolog |
| arsB | 87082277 | arsenite transporter |
| arsC | 1789918 | arsenate reductase |
| arsR | 1789916 | DNA-binding transcriptional repressor |
| beeE | 1787397 | Pseudogene, N-terminal fragment, portal protein |
| borD | 1786770 | bacteriophage lambda Bor protein homolog |
| cohE | 1787391 | CI-like repressor |
| croE | 87081841 | Cro-like repressor |
| cspB | 1787839 | Cold shock protein |
| cspF | 1787840 | Cold shock protein homolog |
| cspI | 1787834 | Cold shock protein |
| cybC | 1790684 | Pseudogene, N-terminal fragment, cytochrome b562 |
| dicA | 1787853 | Regulatory for dicB |
| dicB | 1787857 | Control of cell division |
| dicC | 1787852 | Regulatory for dicB |
| dicF | none | DicF antisense sRNA |
| eaeH | 1786488 | Pseudogene, intimin homolog |
| efeU | 87081821 | Pseudogene reconstruction, ferrous iron permease |
| emrE | 1786755 | multidrug resistance pump |
| essD | 1786767 | predicted phage lysis protein |
| essQ | 87081934 | Phage lambda S lysis protein homolog |
| exoD | 1786750 | Pseudogene, C-terminal exonuclease fragment |
| eyeA | none | novel sRNA, unknown function |
| flu | 48994897 | Antigen 43 |
| flxA | 1787849 | Unknown |

-continued

| Locus | accession number | function |
|---|---|---|
| gapC | 87081902 | Pseudogene reconstruction, GAP dehydrogenase |
| gatR | 87082039 | Pseudogene reconstruction, repressor for gat operon |
| glvC | 1790116 | Pseudogene reconstruction |
| glvG | 1790115 | Pseudogene reconstruction, 6-phospho-beta-glucosidase |
| gnsB | 87081932 | Multicopy suppressor of secG(Cs) and fabA6(Ts) |
| gtrA | 1788691 | Bactoprenol-linked glucose translocase |
| gtrB | 1788692 | Bactoprenol glucosyl transferase |
| gtrS | 1788693 | glucosyl transferase |
| hokD | 1787845 | Small toxic membrane polypeptide |
| icd | 1787381 | Isocitrate dehydrogenase |
| icdC | 87081844 | Pseudogene |
| ilvG | 87082328 | Pseudogene reconstruction, acetohydroxy acid synthase II |
| insA | 1786204 | IS1 gene, transposition function |
| insA | 1786204 | IS1 gene, transposition function |
| insB | 1786203 | IS1 insertion sequence transposase |
| insB | 1786203 | IS1 insertion sequence transposase |
| insC | 1786557 | IS2 gene, transposition function |
| insD | 1786558 | IS2 gene, transposition function |
| insD | 1786558 | IS2 gene, transposition function |
| insE | 1786489 | IS3 gene, transposition function |
| insF | 1786490 | IS3 gene, transposition function |
| insH | 1786453 | IS5 gene, transposition function |
| insH | 1786453 | IS5 gene, transposition function |
| insH | 1786453 | IS5 gene, transposition function |
| insI | 1786450 | IS30 gene, transposition function |
| insI(-1) | 1786450 | IS30 gene, transposition function |
| insM | 87082409 | Pseudogene, truncated IS600 transposase |
| insN | 1786449 | Pseudogene reconstruction, IS911 transposase ORFAB |
| insO | none | Pseudogene reconstruction, IS911 transposase ORFAB |
| insX | 87081710 | Pseudogene, IS3 family transposase, N-terminal fragment |
| insZ | 1787491 | Pseudogene reconstruction, IS4 transposase family, in ISZ' |
| intA | 1788974 | Integrase gene |
| intB | 1790722 | Pseudogene reconstruction, P4-like integrase |
| intD | 1786748 | predicted integrase |
| intE | 1787386 | e14 integrase |
| intF | 2367104 | predicted phage integrase |
| intG | 1788246 | Pseudogene, integrase homolog |
| intK | 1787850 | Pseudogene, integrase fragment |
| intQ | 1787861 | Pseudogene, integrase fragment |
| intR | 1787607 | Integrase gene |
| intS | 1788690 | Integrase |
| intZ | 1788783 | Putative integrase gene |
| isrC | none | Novel sRNA, function unknown |
| jayE | 87081842 | Pseudogene, C-terminal fragment, baseplate |
| kilR | 87081884 | Killing function of the Rac prophage |
| lafU | none | Pseudogene, lateral flagellar motor protein fragment |
| lfhA | 87081703 | Pseudogene, lateral flagellar assembly protein fragment |
| lit | 1787385 | Cell death peptidase |
| lomR | 1787632 | Pseudogene reconstruction, lom homolog; outer membrane protein interrupted by ISSY, missing N-terminus |
| malS | 1789995 | α-amylase |
| mcrA | 1787406 | 5-methylcytosine-specific DNA binding protein |
| mdtQ | 87082057 | Pseudogene reconstruction, lipoprotein drug pump OMF family |
| melB | 1790561 | melibiose permease |
| mmuM | 1786456 | homocysteine methyltransferase |
| mmuP | 870811708 | S-methylmethionine permease |
| mokA | none | Pseudogene, overlapping regulatory peptide, enables hokB |
| ninE | 1786760 | unknown |
| nmpC | 1786765 | Pseudogene reconstruction, OM porin, interrupted by IS5B |
| nohD | 1786773 | DNA packaging protein |
| nohQ | 1787830 | Pseudogene, phage lambda Nul homolog, terminase small subunit family, putative DNA packaging protein |
| ogrK | 1788398 | Positive regulator of P2 growth |
| ompT | 1786777 | outer membrane protease VII |
| oweE | none | Pseudogene, lambda replication protein O homolog |
| oweS | 1788700 | Pseudogene, lambda replication protein O homolog |
| pauD | none | argU pseudogene, DLP12 prophage attachment site |
| pawZ | none | CPS-53 prophage attachment site attR, argW pseudogene |
| pbl | 87082169 | Pseudogene reconstruction, pilT homolog |
| peaD | 87081754 | Pseudogene, phage lambda replication protein P family; C-terminal fragment |
| perR | 1786448 | predicted DNA-binding transcriptional regulator |
| pgaA | 1787261 | Outer membrane porin of poly-β-1,6-N-acetyl-D-glucosamine (PGA) biosynthesis pathway |
| pgaB | 1787260 | PGA N-deacetylase |

-continued

| Locus | accession number | function |
|---|---|---|
| pgaC | 1787259 | UDP-N-acetyl-D-glucosamine β-1,6-N-acetyl-D-glucosaminyl transferase |
| pgaD | 1787258 | predicted inner membrane protein |
| phnE | 87082370 | Pseudogene reconstruction, phosphonate permease |
| pinE | 1787404 | DNA invertase |
| pinH | 1789002 | Pseudogene, DNA invertase, site-specific recombination |
| pinQ | 1787827 | DNA invertase |
| pinR | 1787638 | DNA invertase |
| prfH | 1786431 | Pseudogene, protein release factor homolog |
| psaA | none | ssrA pseudogene, CP4-57 attachment site duplication |
| ptwF | none | thrW pseudogene, CP4-6 prophage attachment site |
| quuD | 1786763 | predicted antitermination protein |
| quuQ | 87081935 | Lambda Q antitermination protein homolog |
| racC | 1787614 | unknown |
| racR | 1787619 | Rac prophage repressor, cI-like |
| ralR | 1787610 | Restriction alleviation gene |
| rbsA | 1790190 | D-ribose ABC transporter subunit (ATP-binding component) |
| rbsD | 87082327 | D-ribose pyranase |
| recE | 1787612 | RecET recombinase |
| recT | 1787611 | RecET recombinase |
| relB | 1787847 | Antitoxin for RelE |
| relE | 1787846 | Sequence-specific mRNA endoribonuclease |
| rem | 1787844 | unknown |
| renD | 87081755 | Pseudogene reconstruction, lambda ren homolog, interrupted by IS3C; putative activator of lit transcription |
| rhsE | 1787728 | Pseudogene, rhs family, encoded within RhsE repeat |
| rnlA | 1788983 | RNase LS, endoribonuclease |
| rph | 1790074 | Pseudogene reconstruction, RNase PH |
| rusA | 1786762 | Endonuclease |
| rzoD | 87081757 | Probable Rzl-like lipoprotein |
| rzoQ | none | Probable Rzl-like lipoprotein |
| rzoR | 87081890 | Probable Rzl-like lipoprotein |
| rzpD | 1786769 | predicted murein endopeptidase |
| rzpQ | 1787835 | Rz-like equivalent |
| rzpR | 87081889 | Pseudogene, Rz homolog |
| sieB | 87081885 | Superinfection exclusion protein |
| sokA | none | Pseudogene, antisense sRNA blocking mokA/hokA translation |
| stfE | 87081843 | C-terminal Stf variable cassette, alternate virion-host specificity protein; Tail Collar domain, pseudogene |
| stfP | 1787400 | Predicted tail fiber protein |
| stfR | 87081892 | Side-tail fiber protein |
| tfaD | 87081759 | Pseudogene, tail fiber assembly gene, C-terminal fragment |
| tfaE | 1787402 | Predicted tail fiber assembly gene |
| tfaP | 1787401 | Predicted tail fiber assembly gene |
| tfaQ | 2367120 | Phage lambda tail fiber assembly gene homolog |
| tfaR | 1787637 | Phage lambda tail fiber assembly gene homolog |
| tfaS | 87082088 | Pseudogene, tail fiber assembly gene, C-terminal fragment |
| tfaX | 2367110 | Pseudogene reconstruction, tail fiber assembly gene, C-terminal fragment |
| thrW | none | threonine tRNA (attachment site of the CP4-6 prophage) |
| torI | 87082092 | CPS-53/KpLE1 exisionase |
| treB | 2367362 | subunit of trehalose PTS permease (IIB/IIC domains) |
| treC | 1790687 | trehalose-6-phosphate hydrolase |
| trkG | 1787626 | Major constitutive K+ uptake permease |
| ttcA | 1787607 | Integrase gene |
| ttcC | none | Pseudogene, prophage Rac integration site ttcA duplication |
| uidB | 1787902 | Glucuronide permease, inactive point mutant |
| uxaA | 1789475 | altronate hydrolase |
| uxaC | 2367192 | uronate isomerase |
| wbbL | 1788343 | Pseudogene reconstruction, rhamnosyl transferase |
| wcaM | 1788356 | predicted colanic acid biosynthesis protein |
| xisD | none | Pseudogene, exisionase fragment in defective prophage DLP12 |
| xisE | 1787387 | e14 excisionase |
| yabP | 1786242 | Pseudogene reconstruction |
| yafF | 87081701 | Pseudogene, C-terminal fragment, H repeat-associated protein |
| yafU | 1786411 | Pseudogene, C-terminal fragment |
| yafW | 1786440 | antitoxin of the YkfI-YafW toxin-antitoxin system |
| yafX | 1786442 | unknown |
| yafY | 1786445 | predicted DNA-binding transcriptional regulator; inner membrane lipoprotein |
| yafZ | 87081705 | unknown |
| yagA | 1786462 | predicted DNA-binding transcriptional regulator |
| yagB | 87081711 | Pseudogene, antitoxin-related, N-terminal fragment |

-continued

| Locus | accession number | function |
|---|---|---|
| yagE | 1786463 | predicted lyase/synthase |
| yagF | 1786464 | predicted dehydratase |
| yagG | 1786466 | putative sugar symporter |
| yagH | 1786467 | putative β-xylosidase |
| yagI | 1786468 | predicted DNA-binding transcriptional regulator |
| yagJ | 1786472 | unknown |
| yagK | 1786473 | unknown |
| yagL | 1786474 | DNA-binding protein |
| yagM | 2367101 | unknown |
| yagN | 2367102 | unknown |
| yagP | 1786476 | Pseudogene, LysR family, fragment |
| yaiT | 1786569 | Pseudogene reconstruction, autotransporter family |
| yaiX | 87082443 | Pseudogene reconstruction, interrupted by IS2A |
| ybbD | 1786709 | Pseudogene reconstruction, novel conserved family |
| ybcK | 1786756 | predicted recombinase |
| ybcL | 1786757 | predicted kinase inhibitor |
| ybcM | 1786758 | predicted DNA-binding transcriptional regulator |
| ybcN | 1786759 | DNA base-flipping protein |
| ybcO | 1786761 | unknown |
| ybcV | 87081758 | unknown |
| ybcW | 1786772 | unknown |
| ybcY | 48994878 | Pseudogene reconstruction, methyltransferase family |
| ybeM | 1786843 | Pseudogene reconstruction, putative CN hydrolase |
| ybfG | 87081771 | Pseudogene reconstruction, novel conserved family |
| ybfI | none | Pseudogene reconstruction, KdpE homolog |
| ybfL | 87081775 | Pseudogene reconstruction, H repeat-associated protein |
| ybfO | 1786921 | Pseudogene, copy of Rhs core with unique extension |
| ycgH | 87081847 | Pseudogene reconstruction |
| ycgI | 1787421 | Pseudogene reconstruction, autotransporter homolog |
| ycjV | 1787577 | Pseudogene reconstruction, malK paralog |
| ydaC | 1787609 | unknown |
| ydaE | 87081883 | Metallothionein |
| ydaF | 87081886 | unknown |
| ydaG | 87081887 | unknown |
| ydaQ | 87081882 | Putative exisionase |
| ydaS | 1787620 | unknown |
| ydaT | 1787621 | unknown |
| ydaU | 1787622 | unknown |
| ydaV | 1787623 | unknown |
| ydaW | 87081888 | Pseudogene, N-terminal fragment |
| ydaY | 1787629 | pseudogene |
| ydbA | 87081898 | Pseudogene reconstruction, autotransporter homolog |
| yddK | 1787745 | Pseudogene, C-terminal fragment, leucine-rich |
| yddL | 1787746 | Pseudogene, OmpCFN porin family, N-terminal fragment |
| ydeT | 1787782 | Pseudogene, FimD family, C-terminal fragment |
| ydfA | 1787854 | unknown |
| ydfB | 87081937 | unknown |
| ydfC | 1787856 | unknown |
| ydfD | 1787858 | unknown |
| ydfE | 1787859 | Pseudogene, N-terminal fragment |
| ydfJ | 1787824 | Pseudogene reconstruction, MFS family |
| ydfK | 1787826 | Cold shock gene |
| ydfO | 87081931 | unknown |
| ydfR | 1787837 | unknown |
| ydfU | 87081936 | unknown |
| ydfV | 1787848 | unknown |
| ydfX | 1787851 | pseudogene |
| yedN | 87082002 | Pseudogene reconstruction, IpaH/YopM family |
| yedS | 87082009 | Pseudogene reconstruction, outer membrane protein homolog |
| yeeH | none | Pseudogene, internal fragment |
| yeeL | 87082016 | Pseudogene reconstruction, glycosyltransferase family |
| yeeP | 87082019 | Pseudogene, putative GTP-binding protein |
| yeeR | 87082020 | unknown |
| yeeS | 1788312 | unknown |
| yeeT | 1788313 | unknown |
| yeeU | 1788314 | Antitoxin component of toxin-antitoxin protein pair YeeV-YeeU |
| yeeV | 1788315 | Toxin component of toxin-antitoxin protein pair YeeV-YeeU |
| yeeW | 1788316 | pseudogene |
| yegZ | none | Pseudogene, gpD phage P2-like protein D; C-terminal fragment |
| yehH | 87082046 | Pseudogene reconstruction |
| yehQ | 87082050 | Pseudogene reconstruction |
| yejO | 1788516 | Pseudogene reconstruction, autotransporter homolog |
| yfaH | 1788571 | Pseudogene reconstruction, C-terminal fragment, LysR homolog |

-continued

| Locus | accession number | function |
|---|---|---|
| yfaS | 87082066 | Pseudogene reconstruction |
| yfcU | 1788678 | Pseudogene reconstruction, FimD family |
| yfdK | 1788696 | unknown |
| yfdL | 1788697 | Pseudogene, tail fiber protein |
| yfdM | 87082089 | Pseudogene, intact gene encodes a predicted DNA adenine methyltransferase |
| yfdN | 1788699 | unknown |
| yfdP | 1788701 | unknown |
| yfdQ | 1788702 | unknown |
| yfdR | 87082090 | unknown |
| yfdS | 1788704 | unknown |
| yfdT | 1788705 | unknown |
| yffL | 1788784 | unknown |
| yffM | 1788785 | unknown |
| yffN | 1788786 | unknown |
| yffO | 1788787 | unknown |
| yffP | 1788788 | unknown |
| yffQ | 1788790 | unknown |
| yffR | 1788791 | unknown |
| yffS | 1788792 | unknown |
| yfjH | 1788976 | unknown |
| yfjI | 1788978 | unknown |
| yfjJ | 1788979 | unknown |
| yfjK | 1788980 | unknown |
| yfjL | 1788981 | unknown |
| yfjM | 1788982 | unknown |
| yfjO | 87082140 | unknown |
| yfjP | 48994902 | unknown |
| yfjQ | 1788987 | unknown |
| yfjR | 1788988 | unknown |
| yfjS | 87082142 | unknown |
| yfjT | 1788990 | unknown |
| yfjU | 1788991 | pseudogene |
| yfjV | 1788992 | Pseudogene reconstruction, arsB-like C-terminal fragment |
| yfjW | 2367146 | unknown |
| yfjX | 1788996 | unknown |
| yfjY | 1788997 | unknown |
| yfjZ | 1788998 | Antitoxin component of putative toxin-antitoxin YpjF-YfjZ |
| ygaQ | 1789007 | Pseudogene reconstruction, has alpha-amylase-related domain |
| ygaY | 1789035 | Pseudogene reconstruction, MFS family |
| ygeF | 2367169 | Pseudogene reconstruction, part of T3SS PAI ETT2 remnant |
| ygeK | 87082170 | Pseudogene reconstruction, part of T3SS PAI ETT2 remnant |
| ygeN | 1789221 | Pseudogene reconstruction, orgB homolog |
| ygeO | 1789223 | Pseudogene, orgA homolog, part of T3SS PAI ETT2 remnant |
| ygeQ | 1789226 | Pseudogene reconstruction, part of T3SS PAI ETT2 remnant |
| yghE | 1789340 | Pseudogene reconstruction, general secretion protein family |
| yghF | 1789341 | Pseudogene, general secretion protein |
| yghO | 1789354 | Pseudogene, C-terminal fragment |
| yghX | 1789373 | Pseudogene reconstruction, S9 peptidase family |
| yhcE | 1789611 | Pseudogene reconstruction, interrupted by IS5R |
| yhdW | 1789668 | Pseudogene reconstruction |
| yhiL | 87082275 | Pseudogene reconstruction, FliA regulated |
| yhiS | 1789920 | Pseudogene reconstruction, interrupted by IS5T |
| yhjQ | 1789955 | Pseudogene reconstruction |
| yibJ | 48994952 | Pseudogene reconstruction, Rhs family |
| yibS | none | Pseudogene reconstruction, Rhs family, C-terminal fragment |
| yibU | none | Pseudogene reconstruction, H repeat-associated protein |
| yibW | none | Pseudogene reconstruction, rhsA-linked |
| yicT | none | Pseudogene, N-terminal fragment |
| yifN | 2367279 | Pseudogene reconstruction |
| yjbI | 1790471 | Pseudogene reconstruction |
| yjdQ | none | Pseudogene reconstruction, P4-like integrase remnant |
| yjgX | 1790726 | Pseudogene reconstruction, EptAB family |
| yjhD | 87082406 | Pseudogene, C-terminal fragment |
| yjhE | 87082407 | Pseudogene, putative transporter remnant |
| yjhR | 1790762 | Pseudogene reconstruction, helicase family, C-terminal fragment |
| yjhV | 1790738 | Pseudogene, C-terminal fragment |
| yjhY | none | Pseudogene reconstruction, novel zinc finger family |
| yjhZ | none | Pseudogene reconstruction, rimK paralog, C-terminal fragment |
| yjiP | 1790795 | Pseudogene reconstruction, transposase family |
| yjiT | 87082428 | Pseudogene, N-terminal fragment |
| yjiV | none | Pseudogene reconstruction, helicase-like, C-terminal fragment |

-continued

| Locus | accession number | function |
|---|---|---|
| YjjN | 87082432 | predicted oxidoreductase |
| ykfA | 87081706 | putative GTP-binding protein |
| ykfB | 1786444 | unknown |
| ykfC | 87081707 | Pseudogene, retron-type reverse transcriptase family, N-terminal fragment |
| ykfF | 1786443 | unknown |
| ykfG | 2367100 | unknown |
| ykfH | 87081704 | unknown |
| ykfI | 1786439 | toxin of the YkfI-YafW toxin-antitoxin system |
| ykfJ | 1786430 | Pseudogene, N-terminal fragment |
| ykfK | 1786445 | Pseudogene, N-terminal fragment |
| ykfL | none | Pseudogene, C-terminal fragment |
| ykfN | none | Pseudogene, N-terminal remnant, YdiA family |
| ykgA | 87081714 | Pseudogene, N-terminal fragment, AraC family |
| ykgP | none | Pseudogene, oxidoreductase fragment |
| ykgQ | none | Pseudogene, C-terminal fragment of a putative dehydrogenase |
| ykgS | none | Pseudogene internal fragment |
| ykiA | 1786591 | Pseudogene reconstruction, C-terminal fragment |
| ylbE | 1786730 | Pseudogene reconstruction, yahG paralog |
| ylbG | 87081748 | Pseudogene reconstruction, discontinuous N-terminal fragment |
| ylbH | 1786708 | Pseudogene, copy of Rhs core with unique extension |
| ylbI | none | Pseudogene, internal fragment, Rhs family |
| ylcG | 87081756 | unknown |
| ylcH | none | unknown |
| ylcI | none | unknown |
| ymdE | 87081823 | Pseudogene, C-terminal fragment |
| ymfD | 1787383 | Putative SAM-dependent methyltransferase |
| ymfE | 1787384 | unknown |
| ymfI | 87081839 | unknown |
| ymfJ | 87081840 | unknown |
| ymfL | 1787393 | unknown |
| ymfM | 1787394 | unknown |
| ymfQ | 1787399 | Putative baseplate or tail fiber proteintt |
| ymfR | 1787396 | unknown |
| ymjC | none | Pseudogene, N-terminal fragment |
| ymjD | none | Expressed deletion pseudogene fusion remnant protein |
| ynaA | 1787631 | Pseudogene, N-terminal fragment |
| ynaE | 1787639 | Cold shock gene |
| ynaK | 1787628 | unknown |
| yncI | 1787731 | Pseudogene reconstruction, H repeat-associated, RhsE-linked |
| yncK | none | Pseudogene reconstruction, transposase homolog |
| yneL | 1787784 | Pseudogene reconstruction, C-terminal fragment, AraC family |
| yneO | 1787788 | Pseudogene reconstruction, putative OM autotransporter adhesi |
| ynfN | 87081933 | Cold shock gene |
| ynfO | none | unknown |
| yoeA | 87082018 | Pseudogene reconstruction, interrupted by IS2F |
| yoeD | none | Pseudogene, C-terminal fragment of a putative transposase |
| yoeF | 87082021 | Pseudogene, C-terminal fragment |
| yoeG | none | pseudogene, N-terminal fragment |
| yoeH | none | pseudogene, C-terminal fragment |
| ypdJ | 87082091 | Pseudogene, exisonase fragment |
| ypjC | 1789003 | Pseudogene reconstruction |
| ypjF | 1788999 | Toxin component of putative toxin-antitoxin pair YpjF-YfjZ |
| ypjI | none | Pseudogene reconstruction |
| ypjJ | 87082144 | unknown |
| ypjK | 87082141 | unknown |
| yqfE | 1789281 | Pseudogene reconstruction, C-terminal fragment, LysR family |
| yqiG | 48994919 | Pseudogene reconstruction, FimD family, interrupted by IS2I |
| yrdE | none | Pseudogene reconstruction, C-terminal fragment, yedZ paralog |
| yrdF | none | Pseudogene, N-terminal fragment |
| yrhA | 87082266 | Pseudogene reconstruction, interrupted by IS1E |
| yrhC | 87082273 | Pseudogene reconstruction, N-terminal fragment |
| ysaC | none | Pseudogene, C-terminal remnant |
| ysaD | none | Pseudogene, internal sequence remnant |
| ytfA | 1790650 | Pseudogene, C-terminal fragment |
| yzgL | 87082264 | Pseudogene, putative periplasmic solute binding protein |

The present invention is also related to the biologically-produced hydroxymethionine such as obtained by the method described above.

The present invention relates also to a composition for animal nutrition, comprising the biologically-produced hydroxymethionine, and to a cosmetic composition comprising the biologically-produced hydroxymethionine.

Recovering of Hydroxymethionine

The action of "recovering hydroxymethionine from the culture medium" designates the action of recovering and purifying hydroxymethionine.

In a specific embodiment of the invention, the hydroxymethionine is recovered from the fermentation broth (culture medium) by extraction.

This recovery might be obtained by liquid-liquid extraction of the fermentation broth. Preferably the solvent used in this extraction is substantially water-immiscible. Suitable solvents are chosen among ketones such as acetone, methyl ethyl ketone, methyl amyl ketone, methyl isoamyl ketone, methyl isopropyl ketone, methyl isobutyl ketone, ethyl butyl ketone, diisobutyl ketone; ethers such as isopropyl ether, tetrahydrofurane and dimethoxyethane, secondary alcohols such as 2-propanol, aldehydes such as n-butyraldehyde and esters such as ethyl acetate, n-butyl acetate, n-proyl acetate and isopropyl acetate. Preferred solvents are chosen among ketone, ethers and secondary alcohols.

In another embodiment of the invention the extraction may be a combination of liquid/liquid extraction and solid/solid extraction.

Hydroxymethionine recovered from the extraction is then purified by distillation, preferably steam distillation, or by evaporation.

Optionally, from 0 to 100%, preferentially at least 90%, more preferentially 95%, even more preferentially at least 99% of the biomass may be retained during the purification of the fermentation product.

DRAWINGS

FIG. 1: Ammonium residual concentrations for culture of strain 1 with the three fedbatch solutions used for the fermentation.

Example I

Construction of Methionine and Hydroxymethionine Producing Strains Tested in Example II 1. Protocols Several protocols have been used to construct methionine and hydroxymethionine producing strains and are described in the following examples.

Protocol 1: Chromosomal Modifications by Homologous Recombination and Selection of Recombinants (Datsenko, K. A. & Wanner, B. L. (2000)

Allelic replacement or gene disruption in specified chromosomal loci was carried out by homologous recombination as described by Datsenko. & Wanner (2000). The chloramphenicol (Cm) resistance cat, the kanamycin (Km) resistance kan, or the gentamycin (Gt) resistance gm genes, flanked by Flp recognition sites, were amplified by PCR by using pKD3 or pKD4 or p34S-Gm (Dennis et Zyltra, AEM July 1998, p 2710-2715) plasmids as template respectively. The resulting PCR product was used to transform the recipient *E. coli* strain harbouring plasmid pKD46 that expresses the λ Red (γ, β, exo) recombinase. Antibiotic-resistant transformants were then selected and the chromosomal structure of the mutated loci was verified by PCR analysis with the appropriate primers.

Protocol 2: Transduction of Phage P1

Chromosomal modifications were transferred to a given *E. coli* recipient strain by P1 transduction. The protocol is composed of 2 steps: (i) preparation of the phage lysate on a donor strain containing the resistance associated chromosomal modification and (ii) infection of the recipient strain by this phage lysate.

Preparation of the Phage Lysate

Inoculate 100 µl of an overnight culture of the strain MG1655 with the chromosomal modification of interest in 10 ml of LB+Km 50 µg/ml+glucose 0.2%+CaCl$_2$ 5 mM (with the antibiotic corresponding to the resistance cassette of the construct).

Incubate 30 min at 37° C. with shaking.

Add 100 µl of P1 phage lysate prepared on the donor strain MG1655 (approx. 1×10$^9$ phage/ml).

Shake at 37° C. for 3 hours until the complete lysis of cells.

Add 200 µl of chloroform, and vortex.

Centrifuge 10 min at 4500 g to eliminate cell debris.

Transfer the supernatant to a sterile tube.

Store the lysate at 4° C.

Transduction

Centrifuge 10 min at 1500 g 5 ml of an overnight culture of the *E. coli* recipient strain cultivated in LB medium.

Suspend the cell pellet in 2.5 ml of MgSO$_4$ 10 mM, CaCl$_2$ 5 mM.

Infect 100 µl cells with 100 µl P1 phage lysate of strain MG1655 with the modification on the chromosome (test tube) and as a control tubes 100 µl cells without P1 phage lysate and 100 µl P1 phage lysate without cells.

Incubate 30 min at 30° C. without shaking.

Add 100 µl sodium citrate 1 M in each tube, and vortex.

Add 1 ml of LB.

Incubate 1 hour at 37° C. with shaking.

Centrifuge 3 min at 7000 rpm.

Plate on LB+Km 50 µg/ml (or the antibiotic corresponding to the resistance cassette)

Incubate at 37° C. overnight.

TABLE 1

Genotype and corresponding number of producing strains showed in the following example.

| Strain number | Genotype |
|---|---|
| 1 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA ::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02- |

TABLE 1-continued

Genotype and corresponding number of producing strains showed in the following example.

| Strain number | Genotype |
|---|---|
| | TTadc-PlambdaR*(-35)-RBS01-thrA*1-cysE-PgapA-metA*11 DtreBC::TT02-serA-serC pJB137-PgapA-pycRe |
| 2 | MG1655 metA*11 Ptrc-metH PtrcF-cysPUWAM PtrcF-cysJIH Ptrc09-gcvTHP Ptrc36-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA ::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC ::Gt Ptrc01-pntAB ::Cm DudhA ::Km |
| 3 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA ::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC DybdL ::Km pCL1920-PgapA-pycRe-TT07 |

2. Construction of strain 1

In order to overexpress the pyruvate carboxylase gene of *Rhizobium etli*, the pJB137-PgapA-pycRe plasmid has been constructed, which is derived from pBluescript-SK (Alting-Mees et al, Nucleic Acids Res. 17 (22), 9494 (1989) and pJB137 plasmid (Blatny et al., Appl. Environ. Microbiol. 63: 370-379, 1997).

To construct the PgapA-pycRe insert, two plasmids have been constructed; pSK-PgapA and pSK-PgapA-pycRe.

First, the gapA promoter and its RBS sequence were amplified from *E. coli* MG1655 genomic DNA using primers Ome 0053-gapA F (SEQ ID No. 1) and Ome 0054-gapA R (SEQ ID No. 2) by PCR. The resulting PCR product was digested by HindIII and cloned between the HindIII sites of plasmid pSK. The obtained plasmid was verified by DNA sequencing and called pSK-PgapA.

Second, the pycRe gene was amplified from *Rhizobium etli* CFN 42 genomic DNA using primers Ome 0057-PycR (SEQ ID No. 3) and Ome058-PycF (SEQ ID No. 4). The resulting PCR product was digested by SmaI and NdeI restrictions enzymes and cloned between the SmaI and NdeI sites of pSK-PgapA plasmid. The obtained plasmid was verified by DNA sequencing and called pSK-PgapA-pycRe.

Finally, the pSK-PgapA-pycRe was digested by SmaI and PsiI restriction enzymes and the resulting PgapA-pycRe digested fragment was cloned between the SmaI sites of pJB137 plasmid. The obtained plasmid was verified by DNA sequencing and called pJB137-PgapA-pycRe.

```
Ome 0053-gapA F
                                                         (SEQ ID NO 1)
ACGTAAGCTTCGTTTAAACAAGCCCAAAGGAAGAGTGAGGC
with
underlined upper case sequence for HindIII and PmeI restriction
sites and extrabases.
upper case sequence homologous to the gapA promoter sequence
(1860640-1860661, reference sequence available on the ECOGENE
website Ome 0054-gapA R
                                                         (SEQ ID NO 2)
ACGTAAGCTTACCGGTCACGTGTCATATGTTCCACCAGCTATTTGTTAG
with
underlined upper case sequence for HindIII, AgeI, AflIII and
NdeI restriction sites and extrabases.
upper case sequence homologous to the gapA promoter sequence
(1860772-1860791, reference sequence available on the ECOGENE
website Ome 0057-PycR
                                                         (SEQ ID NO 3)
ACGTCCCGGGCAAGGACGGGCGAACGAAACC
with
underlined upper case sequence for SmaI restriction site
and extrabases.
upper case sequence homologous to Rhizobium
etli pyruvate carboxylase (pycRe) gene,
(4240368-4240388, reference sequence available on the website of the
National Center for Biotechnology Information (NCBI)

Ome 0058-PycF
                                                         (SEQ ID NO 4)
ACGTACGTAGCATATGCCCATATCCAAGATACTC
with
underlined upper case sequence for SnaBI, NdeI restriction
```

-continued
```
site and extrabases.
upper case sequence homologous to Rhizobium etli pyruvate
carboxylase (pycRe) gene,
except that the GTG start codon of pycRe gene was replaced by
ATG (4236889-4236908, reference sequence available on the National
Center for Biotechnology Information (NCBI) website
```

The pJB137-PgapA-pycRe was introduced by electroporation into the strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6:: TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serC, which has been described in patent applications US20130183727 and US61/406249. The presence of the pJB137-PgapA-pycRe was verified and the selected strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6:: TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC:: TT02-serA-serC pJB137-PgapA-pycRe was called strain 1 (Table 1).

3. Construction of Strain 2

Methionine and hydroxymethionine producer strain 2 (Table 1) has been described in patent applications US20130183727 and U.S. 61/406,249 which is incorporated by reference into this application.

4. Construction of Strain 3

4.1. Construction of MG1655 metA*11 pKD46 dybdL::Km

To delete the ybdL gene in strain MG1655 metA*11 pKD46, Protocol 1 has been used except that primers Ome 0589-DybdLF (SEQ ID No. 5) and Ome 0590-DybdLR (SEQ ID No. 6) have been used to amplify the kanamycin resistance cassette from plasmid pKD4.

```
Ome 0589-DybdLF
                                                      (SEQ ID NO 5)
CACCGACAGCGGAATCGCCGCTACGCCGTGCTCCTGCGTCAGCCACTGG CAAAACTCAACATCATCCAGGGTAGAAACCGTGTAGGCTGGAGCTGCTTCG
with:
upper case sequence homologous to sequence downstream ybdL gene
(633791-633870, reference sequence available on the ECOGENE website
underlined upper case sequence corresponding to the primer
site 1 of pKD4 plasmid
(Datsenko, K.A. & Wanner, B.L., 2000, PNAS, 97: 6640-6645)

Ome 0590-DybdLR
                                                      (SEQ ID NO 6)
GGTACAATAAAAATGACAAATAACCCTCTGATTCCACAAAGCAAACTTCCACA ACTTGGCACCACTATTTTCACCCAGCATATGAATATCCTCCTTAG
with:
upper case sequence homologous to sequence upstream of the ybdL gene
(632797-632874, reference sequence available on the ECOGENE website
underlined upper case sequence corresponding to the primer site
2 of plasmid pKD4 (Datsenko, K.A. & Wanner, B.L., 2000, PNAS,
97: 6640-6645)
```

Kanamycin resistant recombinants were selected. The insertion of the resistance cassette was verified by PCR with primers Ome 0591-ybdLR (SEQ ID No. 7) and Ome 0592-ybdLF (SEQ ID No. 8) and by DNA sequencing. The verified and selected strain was called MG1655 metA*11 AybdL::Km pKD46.

```
Ome 0591-ybdLR
                                                      (SEQ ID NO 7)
CGAAGTGCTGCGCCTGAAGC homologous to sequence upstream of the ybdM gene
(634054-634035, reference sequence available on the ECOGENE website Ome 0592-ybdLF
                                                      (SEQ ID NO 8)
GCCGGGCCGACGACCACGCGG homologous to sequence downstream of the ybdH
gene (632663-632683, reference sequence available on the ECOGENE website
```

4.2. Transduction of the dybdL

The ΔybdL::Km deletion was then transduced into MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6:: TT02-TTadc-PlambdaR*(-35)-RBS01-thrA*1-cysE-PgapA-metA*11 ΔwcaM:: TT02-TTadc-PlambdaR*(-35)-RBS01-thrA*1-cysE-PgapA-metA*11 ΔtreBC:: TT02-serA-serC, which has been described in patent applications US20130183727 and U.S. 61/406,249, by using a P1 phage lysate (Protocol 2) from strain MG1655 metA*11 pKD46 ΔybdL::Km described above in chapter 4.1.

Kanamycin resistant transductants were selected and the presence of the ΔybdL::Km chromosomal modification was verified by PCR with Ome 0591-ybdLR (SEQ ID No. 7) and Ome 0592-ybdLF (SEQ ID No. 8). The resulting strain has the following genotype MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC DybdL::Km.

The pCL1920-PgapA-pycRe-TT07, which has been described in patent applications US20130183727 and U.S. 61/406,249, was introduced by electroporation into that strain. The presence of the pCL1920-PgapA-pycRe-TTO7 was verified and the resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-P lambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-P lambdaR*(-35)-RBS01-thrA*1-cysE-PgapA-metA*11 DtreBC::TT02-serA-serC DybdL::Km pCL1920-PgapA-pycRe-TTO7 was called strain 3 (Table 1).

Example II

Production of Hydroxymethionine by Fermentation with a Fed-Batch Process Under Nitrogen Limitation Strains that produced substantial amounts of metabolites of interest in flask were subsequently tested under production conditions in 2.5 L fermentors (Pierre Guerin) using a fed-batch strategy. The compositions of the different media used are presented in tables 02 to 05.

Briefly, a 24 hour culture grown in 10 mL LB medium with 2.5 g·L$^{-1}$ glucose was used to inoculate a 24 hour preculture in minimal medium (B1a). These incubations were carried out in 500 mL baffled flasks containing 50 mL of minimal medium (B1a) in a rotary shaker (200 RPM). The first preculture was carried out at a temperature of 30° C., the second one at a temperature of 34° C.

A third preculture step was carried out in bio-reactors (Sixfors) filled with 200 mL of minimal medium (B1b) inoculated to a biomass concentration of 1.2 g·L$^{-1}$ with 3 mL concentrated preculture. The preculture temperature was maintained constant at 34° C. and the pH was automatically adjusted to a value of 6.8 using a 10% NH$_4$OH solution. The dissolved oxygen concentration was continuously adjusted to a value of 30% of the partial air pressure saturation with air supply and/or agitation. After glucose exhaustion from the batch medium, fedbatch was started with an initial flow rate of 0.7 mL·h$^{-1}$, increased exponentially for 24 hours with a growth rate of 0.13 h$^{-1}$ in order to obtain a final cellular concentration of about 18 g·L$^{-1}$.

TABLE 2

Preculture batch mineral medium composition (B1a and B1b).

| Compound | B1a Concentration (g · L$^{-1}$) | B1b Concentration (g · L$^{-1}$) |
|---|---|---|
| Zn(CH$_3$COO)$_2$•2H$_2$O | 0.0130 | 0.0130 |
| CuCl$_2$•2H$_2$O | 0.0015 | 0.0015 |
| MnCl$_2$•4H$_2$O | 0.0150 | 0.0150 |
| CoCl$_2$•6H$_2$O | 0.0025 | 0.0025 |
| H$_3$BO$_3$ | 0.0030 | 0.0030 |
| Na$_2$MoO$_4$•2H$_2$O | 0.0025 | 0.0025 |
| Fe(III) citrate H$_2$O | 0.1064 | 0.1064 |
| EDTA | 0.0084 | 0.0084 |
| MgSO$_4$•7H$_2$O | 1.00 | 1.00 |
| CaCl$_2$•2H$_2$O | 0.08 | 0.08 |
| Citric acid | 1.70 | 1.70 |
| KH$_2$PO$_4$ | 4.57 | 4.57 |
| K$_2$HPO$_4$•3H$_2$O | 2.50 | 2.50 |
| (NH$_4$)$_2$HPO$_4$ | 1.10 | 1.10 |
| (NH$_4$)$_2$SO$_4$ | 4.90 | 4.90 |
| (NH$_4$)$_2$S$_2$O$_3$ | 1.00 | 1.00 |
| Thiamine | 0.01 | 0.01 |
| Vitamin B12 | 0.01 | 0.01 |
| Glucose | 30.00 | 5.00 |
| MOPS | 30.00 | 0.00 |
| NH$_4$OH 28% | Adjusted to pH 6.8 | Adjusted to pH 6.8 |

TABLE 3

Preculture fed-batch mineral medium composition (F1)

| Compound | Concentration (g · L$^{-1}$) |
|---|---|
| Zn(CH$_3$COO)$_2$•H$_2$O | 0.0104 |
| CuCl$_2$•2H$_2$O | 0.0012 |
| MnCl$_2$•4H$_2$O | 0.0120 |
| CoCl$_2$•6H$_2$O | 0.0020 |
| H$_3$BO$_3$ | 0.0024 |
| Na$_2$MoO$_4$•2H$_2$O | 0.0020 |
| Fe(III) citrate H$_2$O | 0.0424 |
| EDTA | 0.0067 |
| MgSO$_4$ | 5.00 |
| (NH$_4$)$_2$SO$_4$ | 8.30 |
| Na$_2$SO$_4$ | 8.90 |
| (NH$_4$)$_2$S$_2$O$_3$ | 24.80 |
| Thiamine | 0.01 |
| Glucose | 500.00 |
| Vitamin B12 | 0.01 |
| NH$_4$OH 28% | Adjusted to pH 6.8 |

TABLE 4

Culture batch mineral medium composition (B2).

| Compound | Concentration (g · L$^{-1}$) |
|---|---|
| Zn(CH$_3$COO)$_2$•2H$_2$O | 0.0130 |
| CuCl$_2$•2H$_2$O | 0.0015 |
| MnCl$_2$•4H$_2$O | 0.0150 |
| CoCl$_2$•6H$_2$O | 0.0025 |

TABLE 4-continued

Culture batch mineral medium composition (B2).

| Compound | Concentration (g · L⁻¹) |
|---|---|
| $H_3BO_3$ | 0.0030 |
| $Na_2MoO_4 \cdot 2H_2O$ | 0.0025 |
| Fe(III) citrate $H_2O$ | 0.1064 |
| EDTA | 0.0084 |
| $MgSO_4 \cdot 7H_2O$ | 1.00 |
| $CaCl_2 \cdot 2H_2O$ | 0.08 |
| Citric acid | 1.70 |
| $KH_2PO_4$ | 2.97 |
| $K_2HPO_4 \cdot 3H_2O$ | 1.65 |
| $(NH_4)_2HPO_4$ | 0.72 |
| $(NH_4)_2S_2O_3$ | 3.74 |
| Thiamine | 0.01 |
| Vitamin B12 | 0.01 |
| Glucose | 10 |
| $NH_4OH$ 28% | Adjusted to pH 6.8 |

TABLE 5

Culture fedbatch medium composition (F2, F3 and F4).

| Compound | F2 Concentration (g · L⁻¹) | F3 Concentration (g · L⁻¹) | F4 Concentration (g · L⁻¹) |
|---|---|---|---|
| $Zn(CH_3COO)_2 \cdot 2H_2O$ | 0.0104 | 0.0104 | 0.0104 |
| $CuCl_2 \cdot 2H_2O$ | 0.0012 | 0.0012 | 0.0012 |
| $MnCl_2 \cdot 4H_2O$ | 0.0120 | 0.0120 | 0.0120 |
| $CoCl_2 \cdot 6H_2O$ | 0.0020 | 0.0020 | 0.0020 |
| $H_3BO_3$ | 0.0024 | 0.0024 | 0.0024 |
| $Na_2MoO_4 \cdot 2H_2O$ | 0.0020 | 0.0020 | 0.0020 |
| Fe(III) citrate $H_2O$ | 0.0524 | 0.0524 | 0.0524 |
| EDTA | 0.0067 | 0.0067 | 0.0067 |
| $MgSO_4$ | 5.00 | 5.00 | 5.00 |
| $(NH_4)_2S_2O_3$ | 44.10 | 49.10 | 55.50 |
| Thiamine | 0.01 | 0.01 | 0.01 |
| Vitamin B12 | 0.01 | 0.01 | 0.01 |
| Glucose | 500 | 500 | 500 |
| Ratio C/N of fedbatch medium (Cmole/mole) | 28 | 25 | 22 |
| Ratio C/N of the culture medium (Cmole/mole)* | 25 | 23 | 21 |

*The C/N ratio of culture medium (Cmole/mole) corresponds to the C/N ratio of the culture batch medium (B2) and the fedbatch medium (F2, F3 or F4).

In different media, spectinomycin and kanamycin were added at a final concentration of 50 mg·L⁻¹, chloramphenicol at 30 mg·L⁻¹, carbenicillin at 100 mg·L⁻¹ and gentamicin at 10 mg·L⁻¹ when it was necessary.

Subsequently, 2.5 L fermentors (Pierre Guerin) were filled with 600 mL of minimal medium (B2) and were inoculated to a biomass concentration of 2.1 g·L⁻¹ with a preculture volume ranging between 55 to 70 mL.

The culture temperature was maintained constant at 37° C. and pH was maintained to the working value (6.8) by automatic addition of $NH_4OH$ solutions ($NH_4OH$ 10% for 9 hours and then 28% until the culture end). The initial agitation rate was set at 200 RPM during the batch phase and was increased up to 1000 RPM during the fedbatch phase. The initial airflow rate was set at 40 NL·h⁻¹ during the batch phase and was increased to 100 NL·h⁻¹ at the beginning of the fedbatch phase. The dissolved oxygen concentration was maintained at values between 20 and 40%, preferentially 30% saturation by increasing the agitation.

When the cell mass reached a concentration close to 5 g·L⁻¹, the fedbatch was started with an initial flow rate of 5 mL·h⁻¹. Feeding solution (F2, F3 or F4 according to the experiment) was injected with a sigmoid profile with an increasing flow rate that reached 24 mL·h⁻¹ after 26 hours. The precise feeding conditions were calculated by the equation:

$$Q(t) = p1 + \frac{p2}{1 + e^{-p3(t-p4)}}$$

where Q(t) is the feeding flow rate in mL·h⁻¹ for a batch volume of 600 mL with p1=1.80, p2=22.40, p3=0.270, p4=6.5.

After 26 hours fedbatch, the feeding solution pump was stopped and culture was stopped after glucose exhaustion.

Extracellular amino acids were quantified by HPLC after OPA/Fmoc derivatization and other relevant metabolites were analyzed using HPLC with refractometric detection (organic acids and glucose) and GC-MS after silylation.

In order to enhance hydroxymethionine production we have performed fedbatch fermentations under nitrogen limitation. Cultures were carried out as described above with different fedbatch media called F2, F3 and F4 containing increased ammonium concentrations (see composition in table 5).

With F2 medium, nitrogen limitation occurs around 15 hours of culture time whereas with F3 medium, limitation occurs around 19 hours of culture time. With the F4 fedbatch solution, cells were never under nitrogen limitation conditions.

With F2 and F3 media, final residual ammonium concentrations were close to zero, as confirmed by ionic chromatography measurement presented in FIG. 1 below.

Results presented in table 6 show levels of hydroxymethionine produced by three recombinant strains genetically modified to produce methionine and hydroxymethionine (see genotypes in table 1).

TABLE 6

Final methionine and hydroxymethionine concentrations are indicated in mM for strains 1, 2 and 3 cultivated with different fedbatch solutions. Numbers in bracket indicate culture repetitions.

| | Culture fedbatch media | | | | | |
|---|---|---|---|---|---|---|
| Fermentation product | Strain 1 Methionine (mM) | Strain 1 Hydroxyme thionine (mM) | Strain 2 Methionine (mM) | Strain 2 Hydroxyme thionine (mM) | Strain 3 Methionine (mM) | Strain 3 Hydroxyme thionine (mM) |
| F2 | 291.5 ± 8.2 (N = 3) | 10.5 ± 5.7 (N = 3) | | | 283.4 ± nd (N = 1) | 10.1 ± nd (N = 1) |

TABLE 6-continued

Final methionine and hydroxymethionine concentrations are indicated in mM for strains 1, 2 and 3 cultivated with different fedbatch solutions.
Numbers in bracket indicate culture repetitions.

| | Culture fedbatch media | | | | | |
|---|---|---|---|---|---|---|
| Fermentation product | Strain 1 Methionine (mM) | Strain 1 Hydroxyme thionine (mM) | Strain 2 Methionine (mM) | Strain 2 Hydroxyme thionine (mM) | Strain 3 Methionine (mM) | Strain 3 Hydroxyme thionine (mM) |
| F3 | 309.7 ± 16.5 (N = 4) | 5.7 ± 3.5 (N = 4) | 274.6 ± 6.2 (N = 4) | 1.9 ± 0.3 (N = 4) | | |
| F4 | 310.0 ± 9.5 (N = 3) | 1.2 ± 1.0 (N = 3) | 264.5 ± 13.4 (N = 2) | 1.3 ± 0.1 (N = 2) | 317.1 ± 19 (N = 2) | 1.0 ± 0.6 (N = 2) |

As can be seen, the earlier nitrogen limitation occurs during culture, the more hydroxymethionine production is increased. Strains 1 and 3 cultivated in fedbatch medium F2 produce more than 10 mM of hydroxymethionine but only 1 mM in F4.

REFERENCES

Anderson, 1946, *Proc. Natl. Acad. Sci. USA* 32:120-128.
Carrier and Keasling (1998) Biotechnol. Prog. 15, 58-64.
Datsenko, K. A. & Wanner, B. L. (2000) "One-step inactivation of chromosomal genes in *Escherichia coli* K-12 using PCR products". Proc. Natl. Acad. Sci. USA 97: 6640-6645.
Liebl et al., 1989, *Appl. Microbiol. Biotechnol.* 32: 205-210.
Miller, 1992; "A Short Course in Bacterial Genetics: A Laboratory Manual and Handbook for *Escherichia coli* and Related Bacteria", Cold Spring Harbor Laboratory Press, Cold Spring Harbor, N.Y.
Riedel et al. 2001, *J. Mol. Microbiol. Biotechnol.* 3: 573-583.
J. A. Roels "Energetics and kinetics in biotechnology", Elsevier Science & Technology (May 1983).
Sambrook et al. 1989. "Molecular Cloning: a Laboratory Manual". $2^{nd}$ ed. Cold Spring Harbor Lab., Cold Spring Harbor, N.Y.
Schaefer et al. 1999, *Anal. Biochem.* 270: 88-96.

The invention claimed is:

1. A method for fermentative production of 2-hydroxy-4-(methylthio)butyric acid, comprising three successive steps:
   growing a recombinant microorganism which is one selected from Enterobacteriaceae modified to produce methionine in an appropriate culture medium comprising a source of carbon (C), a source of sulfur (S) and a source of nitrogen (N), and
   culturing said recombinant microorganism under condition of nitrogen limitation in said appropriate culture medium, and
   recovering 2-hydroxy-4-(methylthio)butyric acid from said culture medium.

2. The method according to claim 1, wherein a C/N molar ratio of said culture medium is greater than 5.

3. The method according to claim 1, wherein a C/N molar ratio of said culture medium is greater than about 10.

4. The method according to claim 1, wherein a C/N molar ratio of said culture medium is greater than 20.

5. The method of claim 4, wherein the C/N molar ratio is from about 20 to about 25.

6. The method according to claim 1, wherein said microorganism is cultivated in a bio-reactor system comprising:
   growing said microorganisms for about 10 h to 20 h in an appropriate culture medium comprising a source of carbon, a source of sulphur and a source of nitrogen, and
   culturing said microorganisms for about 10 h to 20 h in nitrogen limitation condition in an appropriate culture medium.

7. The method according to claim 1, wherein said recombinant microorganism comprises at least one of the following genetic modifications:
- increased expression of any of the following genes: metA* encoding a homoserine succinyltransferase with reduced feed-back sensitivity, metH encoding methionine synthase, cysPUWAM encoding respectively periplasmic sulphate binding protein, component of sulphate ABC transporter, membrane bound sulphate transport protein, sulphate permease and an O-acetyl serine sulfhydralase, cysJIH encoding respectively alpha and beta subunits of a sulfite reductase and adenylylsulfate reductase, gcvTHP encoding glycine cleavage complex, metF encoding methylenetetrahydrofolate reductase, serB encoding phosphoserine phosphatase, thrA* encoding aspartokinase/homoserine dehydrogenase with reduced feed-back inhibition, cysE encoding serine acyltransferase, serA encoding phosphoglycerate dehydrogenase, serC encoding phosphoserine aminotransferase, and/or
- attenuated expression of any of the following genes: metJ encoding methionine repressor, pykF encoding pyruvate kinase, pykA encoding pyruvate kinase, purU encoding formyltetrahydrofolate deformylase, yncA encoding N-acetyltransferase, ybdL encoding aminotransferase.

8. The method according to claim 7, wherein said recombinant microorganism further comprises at least one of the following modifications:
- increased expression of the genes pntAB encoding the two subunits of transmembrane pyridine nucleotide transhydrogenase and/or pyc encoding pyruvate carboxylase, and/or
- attenuated expression of the gene udhA encoding nicotinamide nucleotide transhydrogenases.

9. The method according to claim 1, wherein the source of carbon comprises glucose.

10. The method according to claim 1, wherein the source of carbon comprises glucose and sucrose.

11. The method according to claim 1, wherein said sulfur source in the culture medium comprises at least one sulfate, thiosulfate, hydrogen sulfide, dithionate, dithionite, sulfite and/or a combination thereof.

12. The method according to claim 1, wherein said hydroxymethionine is recovered from the culture medium by extraction.

* * * * *

```
                        SEQUENCE LISTING

<160> NUMBER OF SEQ ID NOS: 8

<210> SEQ ID NO 1
<211> LENGTH: 41
<212> TYPE: DNA
<213> ORGANISM: Artificial Sequence
<220> FEATURE:
<223> OTHER INFORMATION: Oligonucleotide

<400> SEQUENCE: 1
acgtaagctt cgtttaaaca agcccaaagg aagagtgagg c                    41

<210> SEQ ID NO 2
<211> LENGTH: 49
<212> TYPE: DNA
<213> ORGANISM: Artificial Sequence
<220> FEATURE:
<223> OTHER INFORMATION: Oligonucleotide

<400> SEQUENCE: 2
acgtaagctt accggtcacg tgtcatatgt tccaccagct atttgttag            49

<210> SEQ ID NO 3
<211> LENGTH: 31
<212> TYPE: DNA
<213> ORGANISM: Artificial Sequence
<220> FEATURE:
<223> OTHER INFORMATION: Oligonucleotide

<400> SEQUENCE: 3
acgtcccggg caaggacggg cgaacgaaac c                              31

<210> SEQ ID NO 4
<211> LENGTH: 34
<212> TYPE: DNA
```

```
<213> ORGANISM: Artificial Sequence
<220> FEATURE:
<223> OTHER INFORMATION: Oligonucleotide

<400> SEQUENCE: 4
acgtacgtag catatgccca tatccaagat actc                                  34

<210> SEQ ID NO 5
<211> LENGTH: 100
<212> TYPE: DNA
<213> ORGANISM: Artificial Sequence
<220> FEATURE:
<223> OTHER INFORMATION: Oligonucleotide

<400> SEQUENCE: 5
caccgacagc ggaatcgccg ctacgccgtg ctcctgcgtc agccactggc aaaactcaac      60
atcatccagg gtagaaaccg tgtaggctgg agctgcttcg                           100

<210> SEQ ID NO 6
<211> LENGTH: 98
<212> TYPE: DNA
<213> ORGANISM: Artificial Sequence
<220> FEATURE:
<223> OTHER INFORMATION: Oligonucleotide

<400> SEQUENCE: 6
ggtacaataa aaatgacaaa taaccctctg attccacaaa gcaaacttcc acaacttggc      60
accactattt tcacccagca tatgaatatc ctccttag                             98

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide

<400> SEQUENCE: 7
cgaagtgctg cgcctgaagc                                                  20

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide

<400> SEQUENCE: 8
gccgggccga cgaccacgcg g                                                21
```